United States Patent
Ahlmén et al.

(10) Patent No.: US 8,205,610 B2
(45) Date of Patent: Jun. 26, 2012

(54) DIFFUSION BARRIER IN A DELIVERY APPARATUS FOR PRESSURIZED MEDICAL LIQUIDS

(75) Inventors: Christer Ahlmén, Sollentuna (SE); Ake Larsson, Järfälla (SE)

(73) Assignee: Maquet Critical Care AB, Solna (SE)

( * ) Notice: Subject to any disclaimer, the term of this patent is extended or adjusted under 35 U.S.C. 154(b) by 1222 days.

(21) Appl. No.: 11/993,272

(22) PCT Filed: Jun. 29, 2005

(86) PCT No.: PCT/EP2005/053068
§ 371 (c)(1),
(2), (4) Date: Dec. 20, 2007

(87) PCT Pub. No.: WO2007/000190
PCT Pub. Date: Jan. 4, 2007

(65) Prior Publication Data
US 2010/0224184 A1    Sep. 9, 2010

(51) Int. Cl.
*A61M 11/00* (2006.01)
*A61M 16/00* (2006.01)
*A61M 15/00* (2006.01)

(52) U.S. Cl. ......... 128/200.21; 128/200.14; 128/200.24; 128/203.12; 128/203.15

(58) Field of Classification Search ........ 128/200.11–200.23, 200.24, 203.12, 128/203.15, 203.16, 203.17, 203.25, 203.26, 128/203.27, 204.14, 204.17, 204.18, 204.21; 239/338, 102.1, 102.2; 261/DIG. 65, 129, 261/154, 70; 73/305–309, 322.5, 448; 604/254; 137/386–454; 122/4 A, 5.5 A, 7 B, 13.01, 122/13.3–19.2, 33, 487, DIG. 7
See application file for complete search history.

(56) References Cited

U.S. PATENT DOCUMENTS

| | | | |
|---|---|---|---|
| 1,411,950 A * | 4/1922 | Wyatt | 261/120 |
| 2,796,294 A | 6/1957 | McKinnon | |
| 4,051,205 A * | 9/1977 | Grant | 261/70 |
| 4,589,282 A * | 5/1986 | Dumery | 73/313 |
| 4,823,827 A * | 4/1989 | Olejak | 137/2 |
| 5,243,973 A * | 9/1993 | Falb et al. | 128/203.27 |
| 6,766,835 B1 * | 7/2004 | Fima | 141/95 |
| 7,731,669 B2 * | 6/2010 | Mathews et al. | 600/585 |
| 7,731,699 B2 * | 6/2010 | Mottola | 604/254 |
| 2003/0066845 A1 * | 4/2003 | Ahlmen et al. | 222/399 |

FOREIGN PATENT DOCUMENTS

DE    386894 C    12/1923

(Continued)

OTHER PUBLICATIONS

"The Oxford Vaporiser No. 2," Cowan et al., The Lancet, vol. 238, Issue 6151, Jul. 19, 1941 (pp. 64-66).

(Continued)

*Primary Examiner* — Annette Dixon
(74) *Attorney, Agent, or Firm* — Schiff Hardin LLP

(57) ABSTRACT

A delivery apparatus for pressurized medical liquids has a reservoir for medical liquid and a pressurizing means configured for pressurizing medical liquid to a driving pressure; with a diffusion barrier arranged to float on medical liquid in the reservoir and disposed to cover substantially the entire surface of the medical liquid in the reservoir for the purpose of preventing diffusion of gas present in the reservoir into the medical liquid.

9 Claims, 2 Drawing Sheets

FOREIGN PATENT DOCUMENTS

| | | |
|---|---|---|
| EP | 1 082 973 A2 | 3/2001 |
| EP | 1 300 172 A1 | 4/2003 |
| GB | 1129194 A | 3/1999 |
| WO | WO89/03483 | 4/1989 |
| WO | WO 99/13228 | 4/1989 |

OTHER PUBLICATIONS

"A New Respirator," Bang, The Lancet, vol. 261, Issue 6763, Apr. 11, 1953 (pp. 723-726).

* cited by examiner

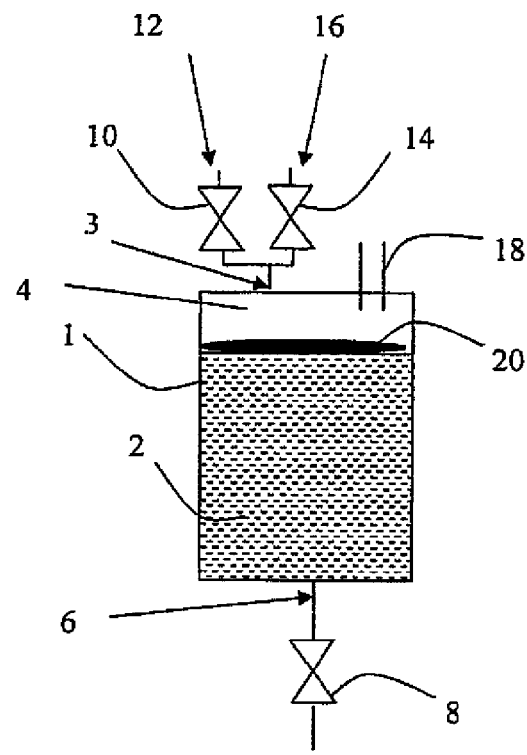
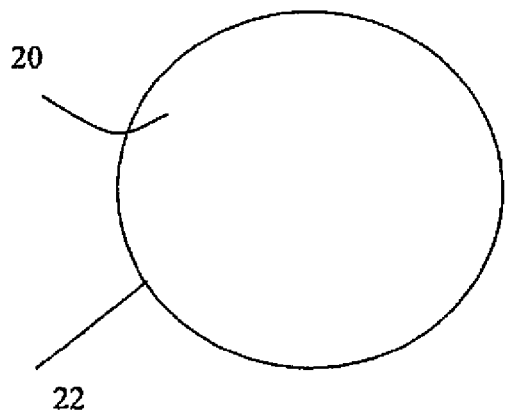
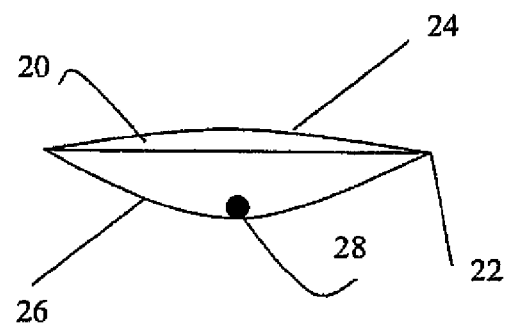
FIG 1
FIG 2A
FIG 2B

DIFFUSION BARRIER IN A DELIVERY APPARATUS FOR PRESSURIZED MEDICAL LIQUIDS

BACKGROUND OF THE INVENTION

1. Field of the Invention

The present invention relates in general to delivery apparatus for pressurized medical liquids and in particular to an apparatus for pressurizing a medical liquid to a delivery pressure.

2. Description of the Prior Art

In delivery apparatuses for pressurized medical liquids it is known to maintain a medical liquid in a reservoir at a delivery pressure by means of pressurized gas. The gas is inlet to the reservoir from a pressurized gas source. In the reservoir the gas exerts its pressure on the surface of the medical liquid and the pressurized liquid is delivered through a controllable outlet. Such an apparatus is used for example in a vaporizer for liquid anesthetic wherein a delivery apparatus delivers the liquid via an injector coupled to the outlet and into a flow of breathing gas. In this kind of use it is important that the delivery apparatus is capable of delivering a certain volume of liquid with a high degree of repeatability.

The basic idea for a delivery apparatus of this kind is that the delivered volume of liquid shall be dependent only on the differential pressure over the controllable outlet and on the time during which the outlet is open. In practice, however, a part of the pressurizing gas dissolves in the liquid, which in its turn affects the delivered volume due to the fact that bubbles of gas appear in the injector and in its inlet ducts as well as in or in the vicinity of possible filters.

Simplified experiments with this type of vaporizer have shown that the delivered volume of liquid deviates with an increase by about 10% when pressurizing gas has been dissolved in the liquid until saturation. More specifically, the medical liquid used in the experiments was anesthetic agent Isofluoran and the pressurizing gas was air. The reservoir was maintained at an overpressure of 1 bar and the pulse time of the injector was set to 2.5 ms (milliseconds). In the experiment the time to saturation of the medical liquid was about 72 hours. It should be noted that these figures are approximate and serve to give a general understanding of the diffusion process in this context.

In clinical practice, vaporizers are often used in lengthy surgical operations during which pressurizing gas thus dissolve in the medical liquid and thereby affects the repeatability and accuracy of the delivered dose of the medical liquid into the breathing gas. In practice an increase of 10% of the anesthetic liquid delivered to the patient would not have a severe effect on the majority of patients. However, it is always an aim for the anesthesiologist to maintain anesthesia with as low dose as possible and to have an accurate control of the process, which is more difficult if the delivered dose increases over time without changing the settings of the apparatus.

Another problem is that bubbles that are created through a pressure drop in the injector can get jammed for some types of injectors.

There is therefore a need for improvement of the repeatability and accuracy of the delivered dose in such a delivery apparatus.

EP1082973 discloses an unaesthetic vaporizer for dosing a liquid anesthetic by means of a liquid pump. This piece of prior art seeks to solve the above mentioned problem of dosing accuracy by pressurizing the anesthetic agent with a liquid pump and a system of regulating means. In addition the apparatus is provided with a return tube in order to make it easier to control pressure downstream from the liquid pump. However, this solution is complicated and expensive due to high demands on the materials used and the limited life span of the used components. Moreover, this prior art does not overcome the problem of diffusion of gas into the anesthetic liquid since the liquid reservoir is connected to an air tube for admitting inlet of air at atmospheric pressure in order to compensate for a negative pressure drop arising when liquid is pumped out of the reservoir.

EP 1 300 172 discloses a delivery apparatus for pressurized liquid anesthetics. In this prior art document a primary reservoir is devised with primary pressurizing means in order to pressurize the liquid to a delivery pressure basically as described in the background section above. The primary reservoir in its turn is connected to a secondary reservoir so as to deliver pressurized liquid to the secondary reservoir. The secondary reservoir is provided with a secondary pressurizing means devised to supply compensating pressure to the liquid in the secondary reservoir in order to maintain it at the delivery pressure when pressure is reduced in the primary reservoir. The purpose is to be able to temporarily allow interruption of the pressurizing activity in the primary reservoir without interruption of delivery of the pressurized liquid from the secondary reservoir. Thereby the primary reservoir can be refilled at atmospheric pressure during operation of the delivery apparatus.

In a first embodiment the secondary pressurizing means involves the arrangement of a movable section in the shape of a membrane that delimits an inner variable volume liquid containing space and that is used to put pressure on the liquid surface by means of a mechanical or pressurized gas biasing force. In fact the secondary reservoir is designed with a function very similar to that of a piston pump, where the movable section corresponds to the piston and there being provided an inlet valve from the primary reservoir and an outlet valve to the injector. Although not explicitly explained in the disclosure of EP 1 300 172, the movable section must be tightly sealed against the inner walls of the secondary reservoir in order to operate properly and maintain the delivery pressure as intended. For the further purpose of achieving a safety seal that prevents evacuation of content in the secondary reservoir, the movable section is provided with a sealing head that is pressed against an outlet when the movable section is moved to reduce the volume of the space to a minimum.

In a second embodiment the secondary pressurizing means is based on a pressurized gas biasing force similar to that of the first pressurizing means for pressurizing the primary reservoir, namely by introducing pressurized gas through a gas port into the space above liquid in the reservoirs. As stated in the description, this embodiment may optionally also be provided with a movable section, in this instance in the shape of a float provided with a sealing surface, for the purpose of sealing the gas port against escape of liquid in case the space of the reservoir is filled with liquid to a maximum level. This may for example occur if the differential pressure between the primary and the secondary reservoirs is accidentally unbalanced with a higher pressure in the primary reservoir than in the secondary reservoir.

Although the float in the secondary reservoir would prevent its liquid content from becoming saturated with pressurizing gas, there is nothing to prevent saturation in the main, primary reservoir. This piece of prior art does not recognize the problem nor provide a solution with regard to repeatability and accuracy of the delivered dose due to diffusion of pressurizing gas in the medical liquid and there is no teaching in EP 1 300 172 that would give guidance to solve that problem.

The article "The Oxford vaporizer No. 2" by S L Cowan et al, The Lancet, vol. 238, issue 6151, 19 Jul. 1941, pages 64-66 discloses a vaporizer for a medical liquid with a small tank provided with a float for the purpose of closing an orifice that leads to a pump in case the level of liquid in the tank falls to a certain level. The purpose is to prevent entry of air into the pump. There is no mentioning of the problem with diffusion of gas into the medical liquid.

The article "A new respirator" by Claus Bang, The Lancet, vol. 261, issue 6763, 11 Apr. 1953, pages 723-726 discloses a respirator apparatus with an automatic valve for controlling the inlet of pressurized breathing gas into the lungs of a patient. The valve is controlled dependent on the pressure of the lungs by means of an arrangement of two connected and liquid filled tubes each being provided with a float. When the pressure in the lungs reaches lower and higher end values, respectively, one of the floats rises to a certain level and connects two electrodes to close an electric circuit that actuates the automatic valve to open or close. The use of floats in this piece of prior art is totally different from that of the present invention.

WO 89/03483 discloses a hydro-pneumatic accumulator of the float type, preferably for use to store energy in connection with a hydraulic system. Hydraulic or hydro-pneumatic accumulators are used in hydraulic systems to receive and deliver large quantities of working fluid during a short time. The accumulator consists of a vertical container, and a free swimming float which serves to separate the accumulator's content and gas and fluid, and to work together with a seal ring in the end cover as a valve which prevents the gas from escaping from the accumulator if it is completely emptied for fluid. This prior art is mainly directed to the problem of providing a float that has a low specific weight and at the same time is strong enough to withstand the high pressures that appear in hydraulic systems. Although this prior art documents deals with problems that are partly similar to those of the present invention, it is not relevant for the skilled person working with anesthesia delivery apparatuses. Those of ordinary skill in the art would not seek solutions from the technical area of high pressure hydraulic systems and therefore this piece of prior art is not relevant as prior art for the present invention.

WO 99/13228 discloses another hydro-pneumatic accumulator for storing pressure in a large volume container for hydraulic oil. The accumulator is provided with a device that separates the fluid area from the gas area. The separating device contains submerging floating bodies arranged on the upper surface of the fluid volume and are situated in the fluid level itself. In addition, the separating device contains at least one protecting body which interacts with the floating bodies and is configured as a shield for further reduction of the contact surface between gas and fluid. This piece of prior art is directed to the problems met in connection with large volume containers and presents a floating device with a separation element mounted on floating bodies. An important issue for this prior art is that the separating device should be possible to introduce through an inspection opening, usually a manhole. As the previously mentioned prior art, this prior art is directed to high pressure and large scale hydraulic system, and for the same reasons it is not relevant as prior art for the present invention.

Thus, none of the prior art addresses the problem of repeatability and accuracy of delivered dose in a medical delivery apparatus with regard to diffusion of pressurizing gas into a medical liquid.

SUMMARY OF THE INVENTION

An object of the present invention is to improve the repeatability and accuracy of the delivered dose in a delivery apparatus for delivering a medical liquid. Aspects of the problem concern the repeatability and accuracy of the delivered dose in a delivery apparatus with medical liquid subjected to gas at atmospheric pressure and gas pressurized medical liquids, respectively.

According to the present invention the problem is solved by prolonging the diffusion time for the gas, i.e. the time it takes the gas to dissolve in the medical liquid until saturation is reached. The problem is perhaps most accentuated in delivery apparatuses operating with pressurizing gas and the invention will therefore mainly be described and discussed in connection with such apparatuses using pressurizing gas, although it is also applicable for gas at atmospheric pressure.

The invention is further based on the fact that time to saturation of a liquid with dissolved pressurizing gas is largely dependent on the size of the area of the liquid surface that is in direct contact with the pressurizing gas. In accordance with the invention a prolonged diffusion time is achieved by minimizing the medical liquid surface area that is in exposed to the pressurizing gas by means of a floating diffusion barrier that is configured to cover substantially the whole surface of the medical liquid in the reservoir. The barrier prevents diffusion of pressurizing gas into the medical liquid.

According to an aspect of the invention, the floating diffusion barrier is configured to enable refilling the reservoir from the top, i.e. from an inlet above the diffusion barrier. For this purpose the diffusion barrier is configured such that there is a suitably sized gap between the diffusion barrier and inner wall of the reservoir to allow medical liquid to pass the diffusion barrier.

According to another aspect of the invention, the floating diffusion barrier is configured to freely follow the surface of the medical liquid as it sinks when doses are delivered and rises when the reservoir is refilled. For this purpose and for the purpose of minimizing the above mentioned gap between the diffusion barrier and the inner wall of the reservoir, the diffusion barrier is preferably shaped as a convex lens with a thin peripheral section in the part of the lens shaped diffusion barrier that is close to the inner wall of the reservoir. This has the effect to prevent the diffusion barrier from sticking to the inner wall of the reservoir in case that the diffusion barrier accidentally gets into an angled position with regard to the horizontal plane of the medical liquid surface.

The latter aspect may be further enhanced by configuring the floating diffusion barrier such that it has a centre of gravity located below the plane defined by the peripheral section and such that the barrier has a balanced floating characteristic.

Yet another aspect of the invention addresses the problem aspect of enabling transport of gas bubbles that occur in the medical liquid past the diffusion barrier.

Furthermore, the diffusion barrier enables refilling of medical liquid in a more controlled way. The barrier will prevent the medical liquid from being stirred up and also prevent bubbles from entering the medical liquid already present in the reservoir.

The invention is advantageously applied in an apparatus for pressurizing a medical liquid to a delivery pressure or directly in a delivery apparatus for such pressurized medical liquids. With a diffusion barrier applied in accordance with the invention the contact surface between the pressurizing gas and the medical liquid is considerably diminished, and thereby the time to saturation is significantly prolonged. Experiments similar to those described above have shown that the time to saturation and in this experiment thereby the time to 10% deviation from the intended dose of the delivered medical liquid with diffusion barrier of the invention is about 480 hours. This a significant difference compared with the prior art type of pressurizing apparatus where the corresponding time to saturation and the time to 10% deviation from the intended dose of the delivered medical liquid is about 72 hours.

BRIEF DESCRIPTION OF THE DRAWINGS

The invention is further explained with reference to the accompanying drawings, in which:

FIG. 1 schematically shows a medical liquid reservoir provided with a surface covering diffusion barrier in accordance with an embodiment of the invention.

FIGS. 2A and 2B show a diffusion barrier in accordance with an embodiment of the invention.

DESCRIPTION OF THE PREFERRED EMBODIMENTS

Figure 3:
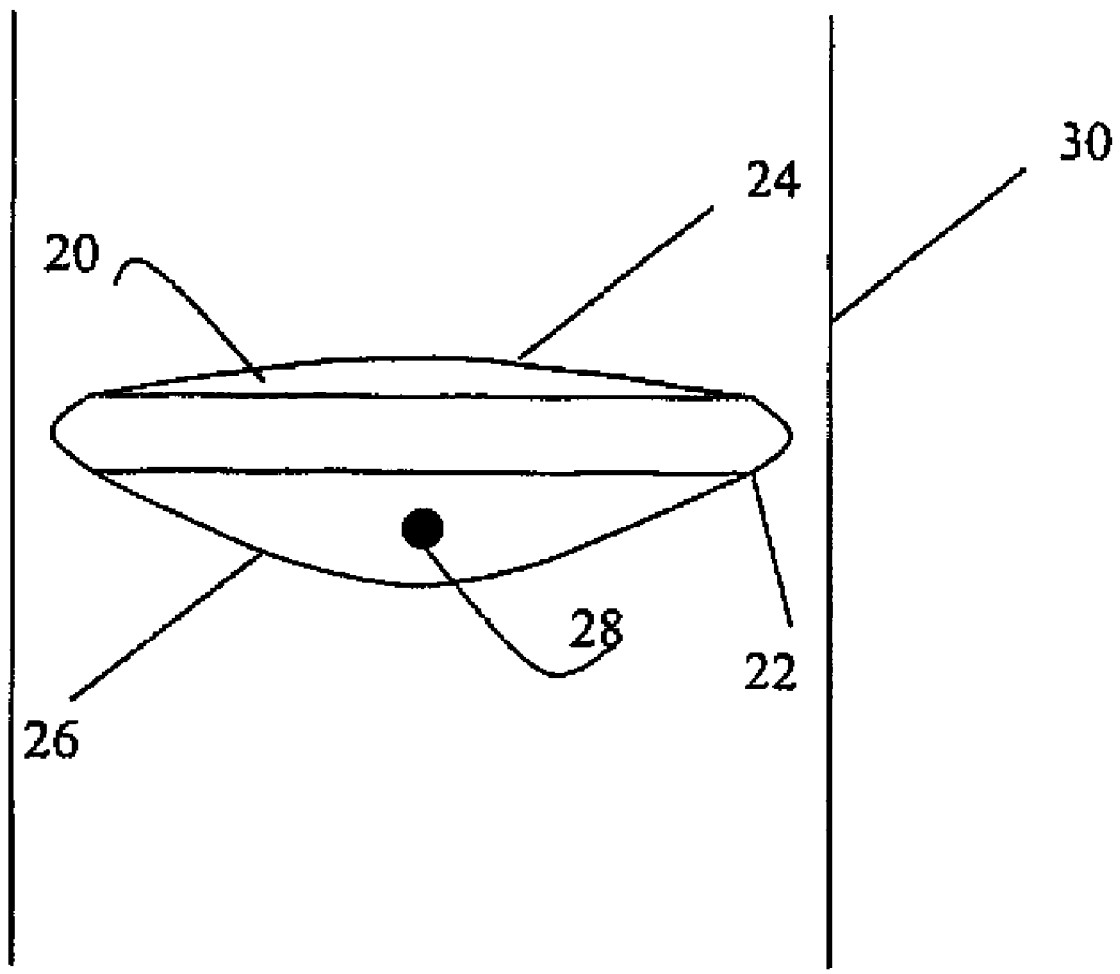
FIG. 3 shows another variety of a diffusion barrier in accordance with the invention.

FIG. 1 shows the invention applied in an apparatus for pressurizing a medical liquid with a reservoir 1 for a medical liquid 2. The reservoir has preferably and exemplified herein the shape of a cylinder. The reservoir 1 is in its upper part provided with an inlet 3 for pressurized gas that is controllably inlet through a gas inlet valve 10 from a source 12 of pressurized gas. The inlet 3 is also used for controllable evacuation of gas from the reservoir through a gas outlet valve 14 to a gas evacuation system 16. The invention is typically applied in an anesthesia system, in which case the gas pressure provided to the reservoir 1 is preferably the driving pressure of the anesthesia system. This driving gas pressure usually has a suitable somewhat higher level than the delivery pressure chosen to fit the individual anesthesia system.

The reservoir 1 is in its lower part provided with an outlet 6 for egress of pressurized medical liquid via a controllable valve 8 that can have a number of functions. The controllable valve 8 may be a safety valve connected to a secondary reservoir for an anesthetic agent, a safety valve connected to an injector for delivering doses of pressurized medical liquid into a flow of breathing gas or be the injector valve itself. The reservoir 1 is further in its upper part provided with a refill inlet 18 provided for refilling the reservoir with medical liquid. The refill inlet is only schematically drawn but would typically be provided with a re-sealable port that can be opened to refill medical liquid preferably under about atmospheric pressure and sealed to withstand the pressurizing pressure from the gas during operation.

The diffusion barrier provided reservoir is preferably intended to be used as a main reservoir in an anesthesia system and could be the primary reservoir, such as in the prior art document EP 1 300 172, having a secondary reservoir close to the dispensing valve, but can of course be used in all systems having pressurized medical liquids without departing from the inventive concept. The main or primary reservoir is generally understood as being the reservoir that stores the main portion of the medical liquid in an anesthesia system, and may or may not be connected for example by tubing to one or a number of secondary reservoirs.

In accordance with the invention a diffusion barrier 20 is provided in the reservoir 1. The diffusion barrier 20 has a horizontal cross-section similar to the horizontal cross-section of the reservoir and is configured to cover substantially the whole surface of the medical liquid in the reservoir. The diffusion barrier 20 floats on the medical liquid surface and separates the medical liquid 2 from the pressurizing gas that gathers in the space 4 above the diffusion barrier 20. During operation the gas exerts pressure on the diffusion barrier 20 that in its turn conveys the pressure to the medical liquid and simultaneously operates as a barrier against diffusion of gas into the medical liquid.

In order to enable refilling of the reservoir with medical liquid entered through the refill inlet at the top of the reservoir there is a suitably sized gap provided between the diffusion barrier 20 and the inner wall of the reservoir. This gap should be minimal but allow medical liquid to pass the surface barrier and gather in the lower part of the reservoir below the diffusion barrier. Furthermore, bubbles may occur when the reservoir is refilled due to the fact that the liquid is mixed with air during the filling process, and also from the pressure drop if the reservoir contains liquid that has been pressurized for a long period of time.

A suitable gap is therefore achieved when there is a circumferential gap that is wide enough to allow medical liquid as well as gas bubbles to pass. With a circular diffusion barrier for a cylindrical reservoir a difference between the inner diameter of the reservoir and the outer diameter of the diffusion barrier in the range of 0.1-1 millimeters may for example be suitable in order to enable a minimal gap while also enabling the diffusion barrier to freely follow the surface of the medical liquid as it sinks when doses are delivered and rises when the reservoir is refilled.

FIGS. 2A and 2B show an embodiment of a diffusion barrier that for this purpose is shaped as a convex lens. FIG. 2A thus shows a top view of a circular diffusion barrier 20 with a circumferential peripheral section 22. FIG. 2B shows a side view of the diffusion barrier 20 with an upper part 24, a lower part 26 and a circumferential peripheral section 22 altogether giving the diffusion barrier the shape of a convex lens.

It is preferable to make the peripheral section of the lens shaped diffusion barrier that is close to the inner wall of the reservoir thin with a hard edge. This shape prevents the diffusion barrier from sticking to the inner wall of the reservoir in case that the diffusion barrier accidentally gets into an angled position with regard to the horizontal plane of the medical liquid surface. However, the peripheral section may also be thick with a maximum radius that is smaller than the inner radius of the cylindrical reservoir. With a thicker peripheral section it is important to adapt the dimension of the peripheral section in relation to a selected dimension of the gap in order to avoid capillary effects that may trap gas bubbles in the passage between the diffusion barrier and inner wall of the reservoir.

This effect is further enhanced in an embodiment as shown in FIG. 2B and wherein the diffusion barrier 20 is configured such that it has a centre of gravity 28 located below the plane defined by the peripheral section and such that the diffusion barrier has a balanced floating characteristic. In the embodiment shown in FIG. 2B the lower part 26 of the convex diffusion barrier is larger than the upper part 24. By this shape a larger proportion of the diffusion barrier material is concentrated to the lower part and the centre of gravity 28 is positioned below the peripheral section plane. It is also conceivable to place a weight in the surface barrier in order to position the centre of gravity, for example in the lowest point of the convex lower part 26 as exemplified in FIG. 2B. This measure counteracts any tendencies for getting stuck in an angling position since the weight in the centre of gravity forms a lever that pulls the diffusion barrier back into a straight position.

FIG. 3 shows another version of the diffusion barrier 20 with a thicker edge placed in a reservoir with schematically shown walls 30. The other reference numbers and features correspond to those of FIGS. 2A-2B described above. The vertical cross section of the edge preferably has the shape of a circle segment with a radius that is smaller than the radius of the circular horizontal cross section of the reservoir. For example, the shape of the diffusion barrier may be that of a sphere with a cut off upper section, slightly smaller than the upper half of the sphere. As in the previously described embodiment, the centre of gravity is placed in the lower part of the diffusion barrier.

The gap and the convex surface of the diffusion barrier serve the purpose of enabling transport of gas bubbles occurring in the medical liquid and preventing bubbles from getting trapped on the lower side of the barrier. In one embodiment the diffusion barrier is treated to have a reduced surface tension for the purpose of enhancing the transport of bubbles from underneath the barrier. It is usually sufficient if the lower side of the barrier has a smooth surface and not too wide an angle towards the reservoir surface, but the selection of material and chemical treatment could be considered.

The figures show a circular cross-section of the reservoir and surface barrier, but an arbitrary cross-section could of course be used without diverting from the inventive concept of reducing the gas saturation. However, the risk of having the diffusion barrier sticking to the wall will have to be dealt with in a manner dependent on the selected cross-section.

The invention has been described above in terms of a general embodiment. However, the invention may be applied in for example the following more specific embodiments.

In one embodiment the invention is applied in an anesthetic vaporizer identical with or similar to that described in EP 1 082 973. For the purpose of description EP 1 082 973 is in its entirety incorporated by reference. In this embodiment the delivery apparatus for pressurized medical liquids comprises a reservoir for medical liquid, where the reservoir is provided with an inlet for admitting inlet of air at atmospheric pressure and an outlet for the medical liquid. The outlet is connected to a pressurizing means in the form of a pump configured for pressurizing medical liquid from the reservoir to a driving pressure. From the pressurizing pump the medical liquid is fed to a dosing point from which doses of medical liquid is delivered at a delivery pressure into a flow of breathing gas. In accordance with the invention, the reservoir is provided with a reservoir diffusion barrier as described above and arranged to float on medical liquid in the reservoir. The diffusion barrier is disposed to cover substantially the whole surface of the medical liquid in the reservoir for the purpose of preventing diffusion of gas present in the reservoir into the medical liquid. In this instance the gas from which the medical liquid is protected is air.

In another embodiment the invention is applied in a delivery apparatus for pressurized medical liquids identical with or similar to that described in EP 1 300 172. For the purpose of description EP 1 300 172 is in its entirety incorporated by reference. In this embodiment the delivery apparatus for pressurized medical liquids comprises a primary and a secondary reservoir for medical liquid. The primary reservoir is provided with a primary pressurizing means configured for pressurizing medical liquid in the primary reservoir to a driving pressure or a delivery pressure. The secondary reservoir has an inlet connected to receive pressurized medical liquid from the primary reservoir and an outlet for egress of the received medical liquid. The secondary reservoir is further provided with secondary pressurizing means arranged for supplying a compensating pressure to the received pressurized medical liquid in order to maintain the pressure at substantially the delivered pressure. In accordance with the invention, the primary reservoir is provided with a reservoir diffusion barrier arranged to float on medical liquid in the primary reservoir. The diffusion barrier is disposed to cover substantially the whole surface of the medical liquid in the primary reservoir for the purpose of preventing diffusion of gas present in the reservoir into the medical liquid. In a variety of this embodiment also the secondary reservoir could be provided with a diffusion barrier. In this instance the pressure is achieved by means of pressurized gas from a pressurized gas source and the gas from which the medical liquid is protected is thus the pressurizing gas.

In general, the invention is applicable in an apparatus for pressurizing a medical liquid wherein the apparatus is a system with a single reservoir, with a first and a second reservoir or a number of reservoirs. The reservoirs may have different configurations and purposes, and may be pressurized by different kinds of pressurizing means. As mentioned above, the diffusion barrier in accordance with the invention is primarily intended to be applied in the main reservoir of the system.

An apparatus for pressurizing a medical liquid in accordance with the present invention can be continuously used for several hours without any significant impact on the accuracy of delivered dose due to diffusion.

Although modifications and changes may be suggested by those skilled in the art, it is the intention of the inventors to embody within the patent warranted heron all changes and modifications as reasonably and properly come within the scope of their contribution to the art.

The invention claimed is:

1. A delivery apparatus for pressurized medical liquids, comprising:
a reservoir containing a medical liquid within an inner wall of said reservoir, said medical liquid having a continuous liquid surface in said reservoir, and a pressurizer that pressurizes a gas above said liquid surface in said reservoir the medical liquid, said reservoir having an upper portion above said continuous liquid surface and a refill inlet disposed in said upper portion allowing refilling of said reservoir with medical liquid, and said reservoir having an outlet located below said liquid surface and a controllable valve in fluid communication with said outlet that controls discharge of said medical liquid, forced by said pressurizer, via said outlet; and
a diffusion barrier that floats unrestrained on the liquid surface on the medical liquid in the reservoir, said diffusion barrier having size that covers said liquid surface of said medical liquid in said reservoir except for a peripheral gap between said inner wall and said diffusion barrier in a range between 0.1 mm and 1 mm, and said diffusion barrier being comprised of a material that, in combination with said size of the diffusion barrier, prevents diffusion of gas in the reservoir into the medical liquid.

2. A delivery apparatus as claimed in claim 1 wherein said pressurizer applies a pressurizing gas to said surface of said medical liquid in said reservoir.

3. A delivery apparatus as claimed in claim 1 wherein said diffusion barrier comprises a horizontal cross-section substantially corresponding to a horizontal cross-section of the reservoir.

4. A delivery apparatus as claimed in claim 1 wherein said reservoir has a cylindrical shape and wherein said diffusion barrier has a shape corresponding to a convex lens.

5. A delivery apparatus as claimed in claim 1 wherein said diffusion barrier has a peripheral section having a vertical cross-section shaped as a segment of a circle having a radius smaller than a radius of a horizontal cross-section of the reservoir.

6. A delivery apparatus as claimed in claim 1 wherein said diffusion barrier has a peripheral section forming a thin ring with a hard edge around said diffusion barrier.

7. A delivery apparatus as claimed in claim 1 wherein said diffusion barrier has a circumferential peripheral section that defines a plane, and a center of gravity located below said plane.

8. A delivery apparatus as claimed in claim 1 wherein said diffusion barrier comprises a surface treatment that reduces a surface tension of said diffusion barrier to promote transport of bubbles in said medical liquid from beneath said diffusion barrier.

9. A delivery apparatus as claimed in claim 1 wherein said reservoir forms a main reservoir of said delivery apparatus.

*